United States Patent
Leung et al.

(10) Patent No.: US 11,929,248 B1
(45) Date of Patent: Mar. 12, 2024

(54) FAR-UVC LIGHT SOURCE WITH AN INTERNAL DIELECTRIC COATING FILTER ARRANGED ON THE INTERIOR SIDE OF ELECTRODE

(71) Applicant: City University of Hong Kong, Kowloon (HK)

(72) Inventors: Kwok Wa Leung, Kowloon (HK); Wai Ki Lee, Yuen Long (HK)

(73) Assignee: City University of Hong Kong

( * ) Notice: Subject to any disclaimer, the term of this patent is extended or adjusted under 35 U.S.C. 154(b) by 0 days.

(21) Appl. No.: 18/321,047

(22) Filed: May 22, 2023

(51) Int. Cl.
| | |
|---|---|
| *H01J 61/06* | (2006.01) |
| *H01J 61/12* | (2006.01) |
| *H01J 61/16* | (2006.01) |
| *H01J 61/34* | (2006.01) |
| *H01J 61/44* | (2006.01) |
| *A61L 2/10* | (2006.01) |

(52) U.S. Cl.
CPC .............. *H01J 61/44* (2013.01); *H01J 61/06* (2013.01); *H01J 61/125* (2013.01); *H01J 61/16* (2013.01); *H01J 61/34* (2013.01); *A61L 2/10* (2013.01); *A61L 2202/11* (2013.01); *H01J 2893/002* (2013.01)

(58) Field of Classification Search
CPC .......... H01J 61/06; H01J 61/125; H01J 61/16; H01J 61/34; H01J 61/44; A61L 2/10
USPC ........................................................ 313/635
See application file for complete search history.

(56) References Cited

U.S. PATENT DOCUMENTS

| | | |
|---|---|---|
| 2015/0073396 A1 | 3/2015 | Randers-Pehrson et al. |
| 2018/0169279 A1 | 6/2018 | Randers-Pehrson et al. |
| 2022/0054689 A1 | 2/2022 | Baxter et al. |

FOREIGN PATENT DOCUMENTS

| | | | |
|---|---|---|---|
| CN | 213716840 | | 7/2021 |
| KR | 2022155080 | A * | 11/2022 |
| WO | 2022043167 | | 3/2022 |

OTHER PUBLICATIONS

EVIO disclosure at http://www.quark-tec.com/en/excimer222-en/.
EVIO leaflet; Quark Technology Co., Ltd.

* cited by examiner

*Primary Examiner* — Christopher M Raabe
(74) *Attorney, Agent, or Firm* — Renner, Kenner, Greive, Bobak, Taylor & Weber (57) ABSTRACT

A Far-UVC excimer light source contains a first electrode adapted to be energized, a second electrode adapted to be energized, a body defining a cavity that is filled with an excited molecule complex between the first and second electrodes; and a Far-UVC optical dielectric coating filter which is a Far-UVC filter attached to the interior side of the first electrode and adapted to filter a Far-UVC light excited in the cavity of the body. The Far-UVC dielectric coating is located inside the light source, between the cavity with the excited molecules and the first electrode. The Far-UVC filter attached to the interior side of the first electrode is a transmissive Far-UVC optical filtering dielectric coating or coated glass which is integrated, placed on, or near the interior side of the first electrode inside the light source.

15 Claims, 6 Drawing Sheets

FAR-UVC LIGHT SOURCE WITH AN INTERNAL DIELECTRIC COATING FILTER ARRANGED ON THE INTERIOR SIDE OF ELECTRODE

FIELD OF INVENTION

This invention relates to Far-ultraviolet-C radiation (Far-UVC) devices, and in particular to Far-UVC excimer lamps.

BACKGROUND OF INVENTION

It is well known that ultraviolet C-radiation light can be used for virus or bacteria disinfection. Ultraviolet C-radiation light is defined in a wavelength between 180 nm and 400 nm. At the lower edge of the UVC band, there is further defined a sub-region called "Far-UVC" which has a wavelength defined in the range of 180 nm-240 nm. As compared to traditional UVC disinfection technologies (such as 254 nm or 275 nm UVC light), Far-UVC light has been proved to be harmless to human skin as there is no penetration.

Recently, Far-UVC excimer lamps attracted a lot of attention. Excimer lamps are a type of light tube containing molecules, or excimers, that can briefly exist in an excited electronic state before returning to their ground state, and in doing so emit UV radiation at various wavelengths in the UVC band depending on the molecules used. Although Far-UVC excimer lamps pose far less danger to human skin by selectively controlling the wavelength of the UVC light, traditional excimer lamps still emit certain percentage of UVC light outside Far-UVC wavelengths and near the 275 nm UVC range. The initial Far-UVC excimer lamps were designed to use an external filter to emit ultraviolet radiation at desired frequency, however the efficiency of such excimer lamps is not very high because of the limitation of the Far-UVC emission efficiency from the excited molecules complex. People are seeking ways to find how to improve the disinfection efficiency.

SUMMARY OF INVENTION

Accordingly, the present invention in one aspect provides a Far-UVC excimer light source. The Far-UVC excimer light source contains at least two electrodes including a first electrode adapted to be energized, and a second electrode adapted to be energized. The Far-UVC excimer light source further contains a body defining a cavity that is filled with an excited molecule complex between the first and second electrodes; and a Far-UVC optical dielectric coating filter which is a Far-UVC filter attached to the interior side of the first electrode and adapted to filter a Far-UVC light excited in the cavity of the body, wherein the Far-UVC dielectric coating is located inside the light source, between the cavity with the excited molecules and the first electrode. The Far-UVC filter attached to the interior side of the first electrode is a transmissive Far-UVC optical filtering dielectric coating or coated glass which is integrated, placed on or near the interior side of first electrode inside the light source.

In some embodiments, the unfiltered Far-UVC light excited in the cavity body of the light source will pass through the transmissive electrode and its attached Far-UVC filter to the exterior environment. A filtered Far-UVC light can be obtained just to emit out from the light source.

In some embodiments, at least one of the electrodes can also be configured to further reflect the unfiltered Far-UVC light excited in the cavity of the light source. Therefore, this reflection will filter the unfiltered Far-UVC light two times through the Far-UVC filter placed on the first electrode. As the light will be emitted mostly in the region of the excited medium of the light source near the highly solid electrode, it would attract more emitted light to the electrode side and be reflected out through the Far-UVC filter by two times back and forth. A further filtered Far-UVC light would be received from the light source without an external component.

In some embodiments, the first electrode is at least partially made of a net metal to transmit the Far-UVC light through its attached Far-UVC dielectric coating filter inside the light source.

In some embodiments, the first electrode is at least partially made of a solid metal to reflect the Far-UVC light through its attached Far-UVC dielectric coating filter inside the light source.

In some embodiments, the Far-UVC filter attached to one of the electrodes is a transmissive Far-UVC optical filtering dielectric coating or coated glass that includes a dielectric coating, which contains dielectric materials with a different refractive index to the substrate. These coatings are constructed from thin layers of dielectric materials such as magnesium fluoride, calcium fluoride, and various metal oxides, In some embodiments, the Far-UVC filter is adapted to filter at least one radiation having wavelengths that are in a range of between 180 nm to 240 nm, and to facilitate a substantial power reduction of the at least one radiation from having wavelengths outside of the range.

In some embodiments, the molecules complex contains at least one of a krypton-bromine gas or a krypton-chlorine gas.

In some embodiments, the body further contains a first tube part and a second tube part that are concentrically arranged, such that the cavity is formed between the first and second tube parts and has a hollow cylindrical shape. The first tube part encloses the second tube part and the cavity. The second electrode is located within the second tube part; the first electrode located outside the first tube part and having a shape that follows a shape of part of the first tube part in a circumferential direction.

In some embodiments, both the first and second electrodes are made of net metals.

In some embodiments, both the first and second electrodes are made of Far-UVC reflective solid metals.

In some embodiments, the first electrode is made of two parts: one part is Far-UVC reflective solid metal and another part is net metal.

In some embodiments, the first electrode is configured further as a heatsink for the Far-UVC excimer light source.

According to another aspect of the invention, there is provided a Far-UVC excimer lamp device, which includes two Far-UVC excimer lamps as described above, and an infrared light source.

In some embodiments, the two Far-UVC excimer lamps and the infrared light source are aligned substantially alone a straight line such that light emission directions from the two Far-UVC excimer lamps and the infrared light source are substantially facing a same direction.

The above embodiments could be combined the part of transmissive electrode and part of reflective electrode into one electrode to perform the filtering reflection and filtering transmission, by its attached Far-UVC dielectric coating filter.

In addition, in embodiments of the invention, with the reflector component integrated with an electrode, the filtering and reflecting can be achieved in the lamp whilst keeping a compact size of the lamp. The compact size will help a same casing of a Far-UVC lamp to receive more Far-UVC tubes to enhance the radiations. Also, the compact size makes it easier to place extra components such as an infrared light source in one embodiment near the Far-UVC tube.

BRIEF DESCRIPTION OF FIGURES

The foregoing and further features of the present invention will be apparent from the following description of embodiments which are provided by way of example only in connection with the accompanying figures, of which:

FIG. 1b shows the perspective view of the first conventional Far-UVC excimer lamp of FIG. 1a.

FIG. 2b shows the perspective view of the second conventional Far-UVC excimer lamp of FIG. 2a.

FIG. 3b shows the perspective view of the Far-UVC excimer lamp of FIG. 3a.

FIG. 4b shows the perspective view of the Far-UVC excimer lamp of FIG. 4a.

FIG. 5b shows the perspective view of the Far-UVC excimer lamp of FIG. 5a.

DETAILED DESCRIPTION

It is known that in general, a Far-UVC excimer light source contains at least two electrodes and a cavity containing excited molecules complex for exciting Far-UVC light.

Figure 1A:
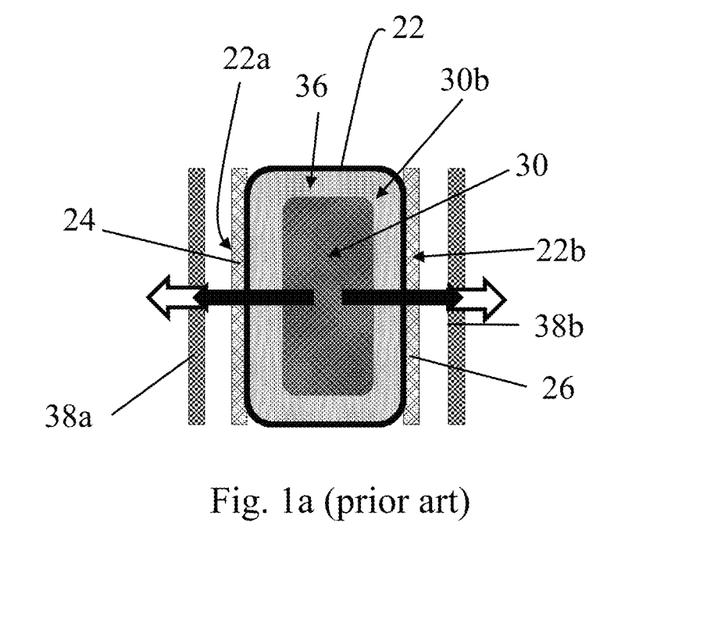
FIG. 1a is a cross-sectional view of a first conventional Far-UVC excimer lamp with external Far-UVC filters, with its working principle also illustrated.
Figure 1B:
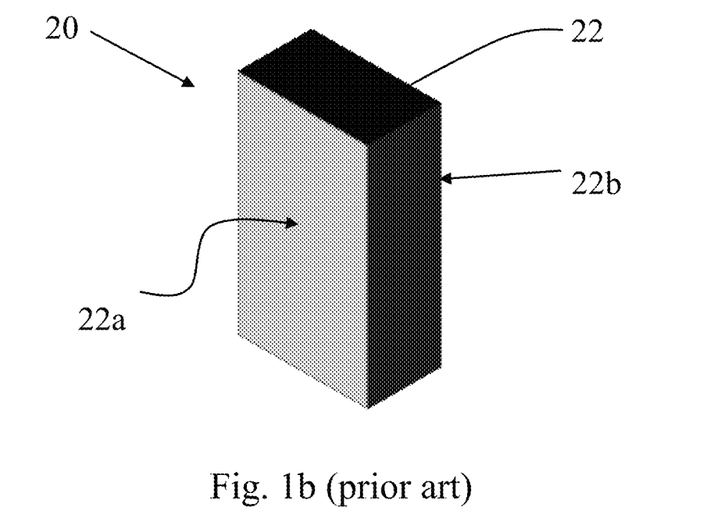

FIGS. 1a-1b show a first conventional Far-UVC excimer lamp 20 that has a substantially elongated shape. The lamp 20 has a body 22 which defines a first end 22a and a second end 22b along the longitudinal direction of the lamp 20. As shown in FIG. 1a, inside the body 22 there is defined a cavity 36 which is filled with an excited molecule complex (not shown) as an excited medium to produce Far-UVC light. The cavity 36 is made of Far-UVC optical transmission glass, such as quartz for allowing Far-UVC light to pass through. The excited molecule complex for example can be an exciplex such as either krypton-bromine (KrBr) or krypton-chlorine (KrCl) for Far-UVC, and the exciplex is in gaseous form. On the other hand, a first electrode 24 is located outside the cavity 36 at the first end 22a of the body 22. A second electrode 26 is located outside the cavity 36 at the second end 22b of the body 22. As shown in FIG. 1a, both the first electrode 24 and the second electrode 26 are positioned against their respective end face of the body 22. The first electrode 24 and the second electrode 26 are separated away from each other, thus the cavity 36 and in turn the excited gas stored in the cavity 36 are located substantially between the first electrode 24 and the second electrode 26. As shown in FIG. 1a, between the first electrode 24 and the second electrode 26 there can be defined a main EM (electromagnetic) field area of radiation 30 and a weak EM field area of radiation 30b which are developed in excited gas. The main EM field area 30 is at a center of the cavity 36 between the first electrode 24 and the second electrode 26.

For the prior art Far-UVC excimer lamp shown in FIGS. 1a-1b, an external transmissive Far-UVC optical filter 38a (which is shown in FIG. 1a only) is arranged outside the body 22, and on the same side of the body 22 as the first electrode 24, but further away from the body 22 than the first electrode 24. Similar, an external transmissive Far-UVC optical filter 38b is arranged outside the body 22, and on the same side of the body 22 as the second electrode 26, but further away from the body 22 than the second electrode 26. The Far-UVC is excited in the cavity 36 through the first electrode 24 and the second electrode 26 to leave the light source. The Far-UVC light in a wavelength of 222 nm will be filtered out from other unwanted light having a wavelength above 230 nm by a certain percentage by the Far-UVC optical filters 38a, 38b.

Figure 2A:
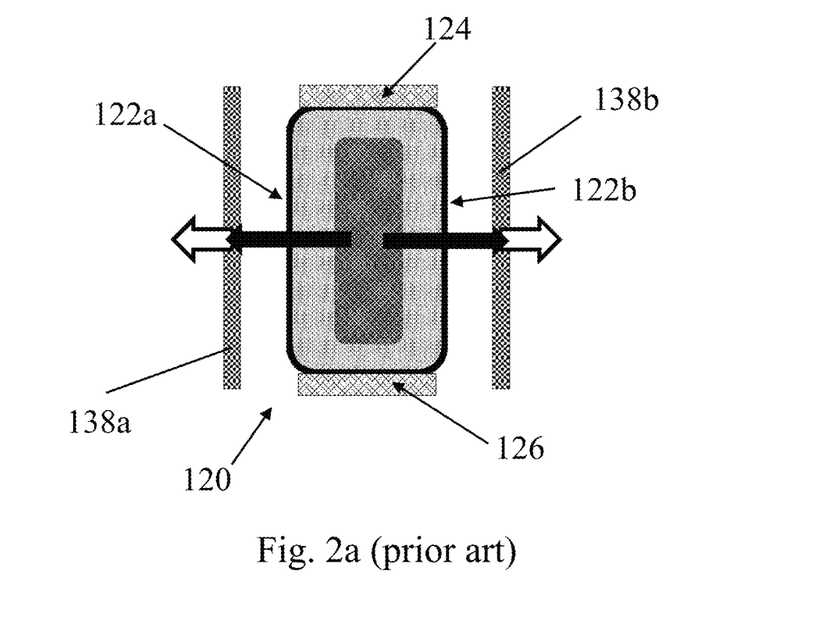
FIG. 2a is a cross-sectional view of a second conventional Far-UVC excimer lamp with external Far-UVC filters, with its working principle also illustrated.
Figure 2B:
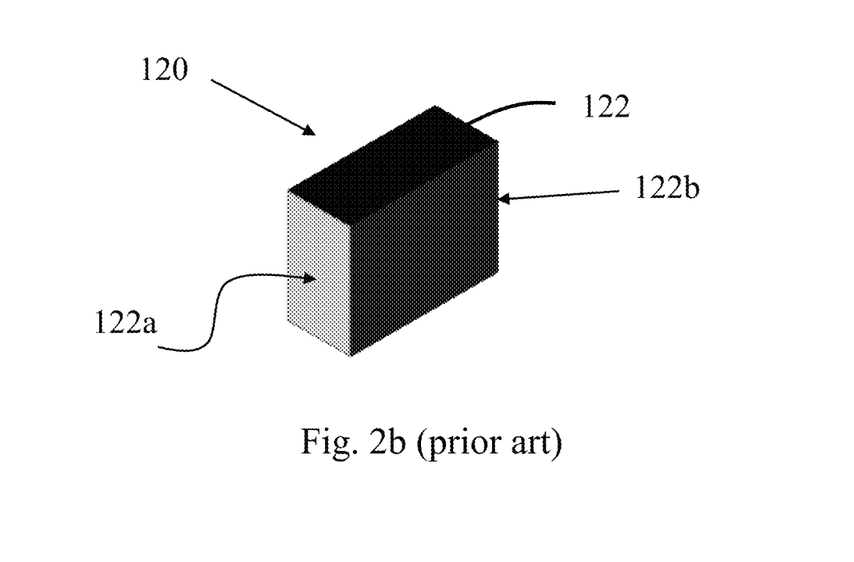

FIGS. 2a-2b show a second conventional Far-UVC excimer lamp 120 that is generally similar to that shown in FIGS. 1a-1b. The lamp 120 similarly has two ends 122a, 122b defined by a body 122 that contains a cavity 136. However, compared to the excimer lamp in FIGS. 1a-1b, the lamp 120 has its electrodes 124, 126 located on other elongated sides of the body 122 that are different from the sides on which the Far-UVC optical filters 138a, 138b are located. Also, the electrodes 124, 126 are shorter as compared to those in FIGS. 1a-1b in order to filter the excited Far-UVC light by the external Far-UVC filters 138a, 138b without the light passing through the electrodes 124, 126.

Figure 3A:
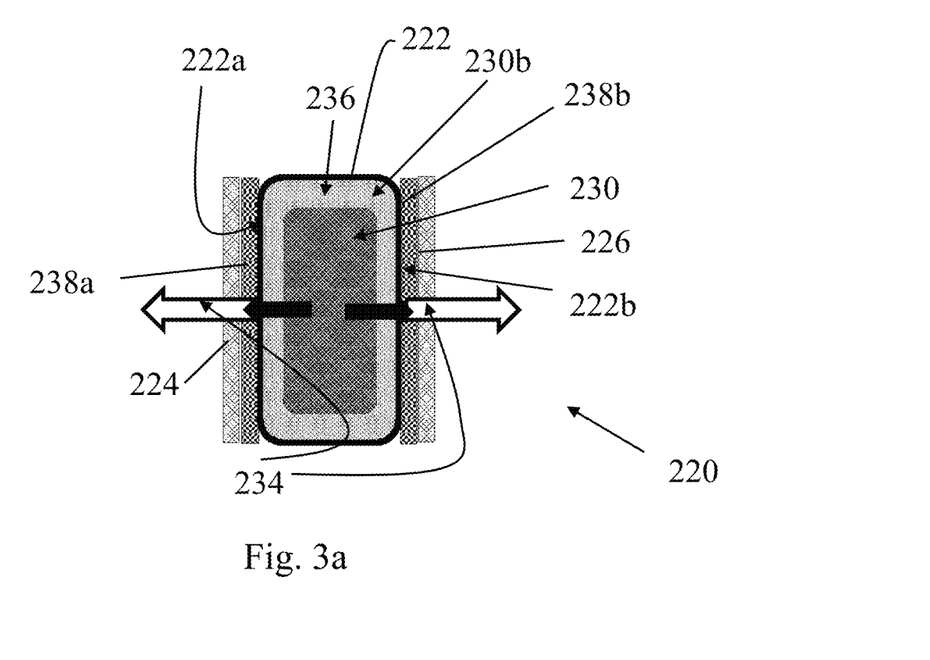
FIG. 3a is a cross-sectional view of a Far-UVC excimer lamp with transmissive dielectric coating filters attached to the interior sides of net metal electrodes, and working principle of the excimer lamp, according to a first embodiment of the invention.
Figure 3B:
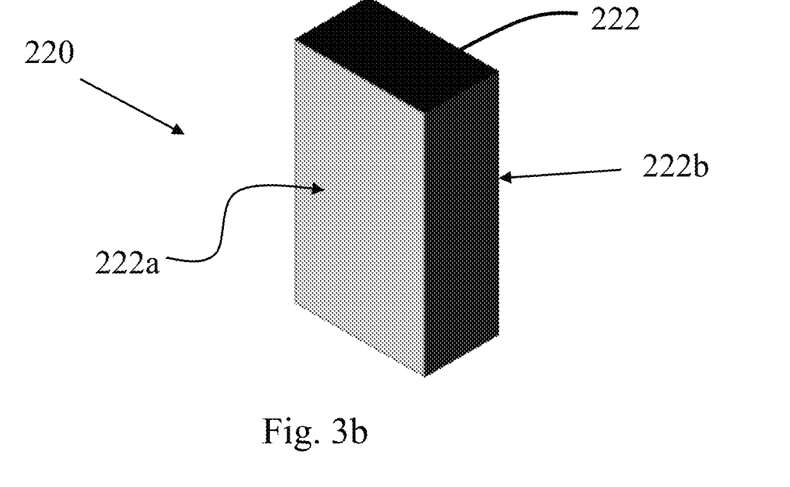

Turning to FIGS. 3a-3b which show a first embodiment of the invention. Compared to the prior art described above, the Far-UVC excimer lamp 220 in this embodiment does not contain an external Far-UVC filter located outside of a body 222 of the Far-UVC excimer lamp 220. Instead, a dielectric filter coating or coated glass is attached to interior sides of the first electrode 224 and the second electrode 226 of the Far-UVC excimer lamp 220. In particular, a Far-UVC optical transmission filtering dielectric coating is integrated, placed on or near the interior sides of both the first electrode 224 and the second electrode 226. In the example shown in FIG. 3a, a Far-UVC optical transmission filtering dielectric coating 238a is placed at the interior side of the first electrode 224, and a Far-UVC optical transmission filtering dielectric coating 238b is placed at the interior side of the first electrode 226. The Far-UVC optical transmission filtering dielectric coatings 238a, 238b are located respectively at a first end 222a and a second end 222b of the body 222.

In a variation of the above embodiment, the Far-UVC optical transmission filtering dielectric coating 238a, 238b is coated on a UVC transmissive glass (not shown) placed at or near the interior side of the first electrode 224 and/or the second electrode 226. In another variation of the embodiment, the Far-UVC optical transmission filtering dielectric coatings 238a, 238b is coated on exterior sides of the body 222 near or touching the first electrode 224 and/or the second electrode 226. In a further variation of the embodiment, the Far-UVC optical filtering dielectric coating 238a, 238b is coated on an interior side of a substrate (not shown) supported by the first electrode 224 and/or second electrode 226. Note that the major type of Far-UVC optical transmission filtering dielectric coating is a kind of dielectric coating using dielectric materials with a different refractive index compared to the substrate. These coatings are constructed from thin layers of dielectric materials such as magnesium fluoride, calcium fluoride, and various metal oxides. Moreover, both the first electrode 224 or the second electrode 226 are made of metallic net conductive material, and the material for the first electrode 224 and the material for the second electrode 226 can be the same or different conductive metals. In one example both the first electrode 224 and the second electrode 226 are made of aluminum net.

Having described the structure of the Far-UVC excimer lamp 220, now the working principle of the Far-UVC excimer lamp 220 will be described. The first electrode 224 and the second electrode 226 are energized when they are connected to an external power supply of the excimer lamp 220, and the first electrode 224 or the second electrode 226 have alternating polarities. When the first electrode 224 and the second electrode 226 are energized, due to the electric field generated therebetween a discharge occurs, generating excimer molecules. When these excited molecules return to their ground state, high-energy ultraviolet light is emitted from the cavity 236 outwards along arrows 234 shown in FIG. 3a. In this embodiment, most of the Far-UVC light (say over 90%) is emitted from the main EM field area of radiation 230 (see FIG. 3a) which has a wavelength between 180-240 nm mainly, and some of the Far-UVC lights (say less than 10%) is emitted from the weak EM field area of radiation 230b (see FIG. 3a). Preferably, the main EM field area of radiation 230 can be tuned to achieve an optimum matching with the complex molecules to acquire more Far-UVC light emission and fewer Far-UVC light emission. As such, the tuned main EM field area of radiation 230 will excite higher purity of Far-UVC lights than the light excited from the weak EM field area of radiation 230b.

It should be noted that the reflection of Far-UVC light may happen multiple times between the first electrode 224 and the second electrode 226, because of the opposite positions of the first electrode 224 and the second electrode 226. However, eventually the reflected and filtered light will leave the body 222 as shown by the arrows 234 in FIG. 3a, and emits as an output of the lamp 220 to the exterior environment, for example to a disinfection target like an object, a surface, or a human. At the same time the structure of the lamp 220 is quite compact and as no additional reflective component like a mirror is required. The compactness is also realized by the first electrode 224 simultaneously functioning as a heatsink (as it is made of solid material like aluminum), and this allows effective heat dissipation during the operation of the lamp 220, so that the separations between components of the lamp 220 can be reduced without the heat imposing any impacts to the stability and lifetime of these components.

The transmissive Far-UVC optical dielectric coatings 238a, 238b are attached to interior sides of the first electrode 224 and the second electrode 226 of the Far-UVC source, and are located in the weak EM field area 230b inside the cavity 236 of the body 222. As the dielectric coatings 238a, 238b are inserted between two the energized electrodes 224 and 226, within inside the generated EM field area of radiation 230 and 230b, the total strength of the EM field area of radiation 230 and 230b can be maintained without distortion.

As the transmissive Far-UVC optical dielectric coatings 238a, 238b are located in the weak EM field of radiation 230b, the Far-ultraviolet light as they are just mostly generated in the main EM field area of radiation 230 pass through the attached Far-UVC optical dielectric coatings 238a, 238b to travel generally toward the first electrode 224 and/or the second electrode 226, both of which are made of net metal as mentioned above, as shown by the arrows 234, and the light is then filtered as always. For different sizes of the cavity 236 with the molecules, if appropriate electrical energizing power is applied to the electrodes 224, 226 and appropriate combination of the molecules complex is allocated, then there is an optimum distance required for the distance between two electrodes 224, 226 for exciting the maximum illumination of the Far-UVC excited from the EM field area of radiation 230 and 230b. As the dielectric constant of the Far-UVC optical dielectric coatings 238a, 238b is higher than the dielectric constant of the gas of molecules complex, the optimum distance is supposed to be shorter and the size of the main EM field area of radiation 230 will not be smaller, thus the illumination is still maintained at the same level. As a result, the configuration of the lamp 220 will be more compact than conventional designs shown in FIGS. 1a-2b comparatively.

As can be seen from FIG. 3a, the distance of the weak EM field area of radiation 230b is shorter than prior art. After it passes through the Far-UVC optical dielectric coatings 238a, 238b and the electrodes 224, 226, the illumination at the surface of the electrodes 224, 226 just coming out from the light source, will be higher than the illumination at the surface of the external filter in the prior art (e.g., those shown in FIGS. 1a-2b). According to the inverse law, it is known that when the light is exposed to the target closer, it will have a higher light exposure level to the target that increases exponentially. If the UVC lamp disinfects a target by a closer distance, the disinfection time will be much shorter, due to the theory of inverse law and lower propagation loss in the atmosphere of the exterior environment by the distance. It implies that the lamp 220 in this embodiment will have a higher disinfection ability than prior art if infect the target very close, hence to have faster disinfection.

In this embodiment, Far-UVC light in a wavelength of 222 nm will be filtered out from other unwanted light having a wavelength above 230 nm by a certain percentage. In one specific example, the transmissive Far-UVC optical dielectric coatings 238a, 238b act as a bandpass filter, and are configured for filtering out Far-UVC radiations substantially in wavelengths in the range of 240 nm-280 nm. In this way, high purity of Far-UVC light can be obtained. In another implementation, the transmissive Far-UVC optical dielectric coatings 238a, 238b filter at least one radiation having wavelengths that are in a range of 180 nm to 240 nm, and facilitate a substantial power reduction of at least one radiation from having wavelengths outside of the range.

Figure 4A:
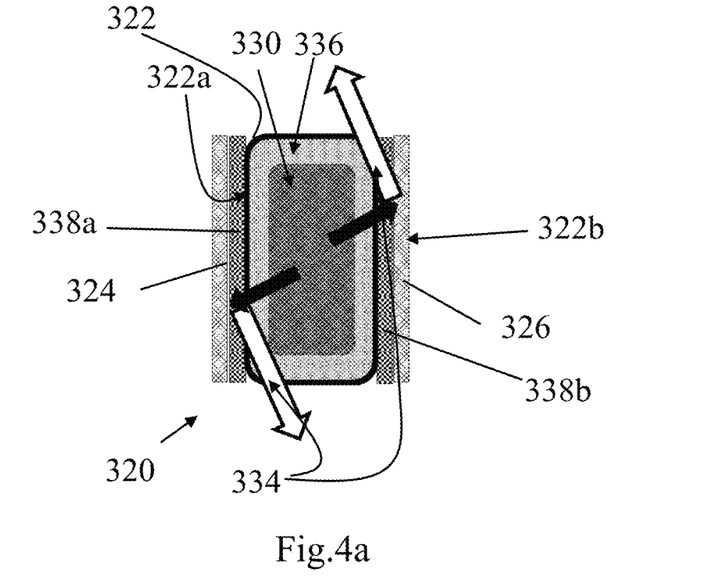
FIG. 4a is a cross-sectional view of a Far-UVC excimer lamp with transmissive dielectric coating filters attached to the interior sides of Far-UVC reflective solid electrodes, and working principle of the Far-UVC excimer lamp, according to a second embodiment of the invention.
Figure 4B:
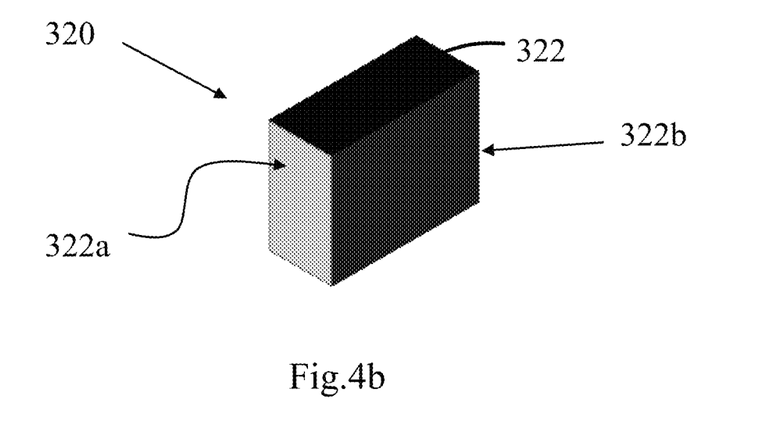

Based on the idea of dielectric filters attached to the electrodes, another embodiment of the invention is shown in FIGS. 4a-4b, which is a Far-UVC excimer lamp 320 having a similar structure as that in FIGS. 3a-3b. However, there is a difference in the mechanism of the lamp 320 as compared to that in FIGS. 3a-3b in that the lamp 320 contains a dielectric coating filter 338a, 338b attached to a reflective first electrode 324 and a reflective second electrode 326. Because of the reflections at the interior sides of the electrodes 324, 326, the Far-UVC light as they are generated in a cavity 336 of the body 322 leave the body 322 at different ends of the body 322 which are not the first end 322a and the second end 322b shown in FIG. 4a, as compared to the light path in FIG. 3a. The reflected direction of the light emission is shown by arrows 334 in FIG. 4a.

The main difference of the electrodes 324, 326 as compared to those in FIG. 3a is that both the first electrode 324 and/or the second electrode 326 are made of solid metal material, and the material for the first electrode 324 and the material for the second electrode 326 can be the same or different. In one example both the first electrode 324 and the second electrode 326 are made of solid aluminum. There is further a transmissive Far-UVC optical dielectric coating filter attached to the interior side of each one of the first electrode 324 and/or the second electrode 326. The Far-UVC optical dielectric coating 338a is attached to the interior side of the first electrode 324, and the Far-UVC optical dielectric coating 338b is attached to the interior side of the second electrode 326.

Regarding the working principle of the Far-UVC excimer lamp 320, it is noted the first electrode 324 and the second electrode 326 are energized when they are connected to an external power supply of the lamp 320, and the first electrode 324 or the second electrode 326 have alternating polarities. When the first electrode 324 and the second electrode 326 are energized, due to the electric field generated between the electrodes a discharge occurs, generating excimer molecules. When these excited molecules return to their ground state, high-intensity Far-UVC light is emitted. In this embodiment, the light emitted from the main EM field area of radiation 330 has a wavelength between 180-240 nm mainly.

The Far-ultraviolet light as they are just generated in the main EM field area of radiation 330 travel generally toward the first electrode 324 and the second electrode 326, as shown by the arrows 334 in FIG. 4a. This is because within the main EM field area of radiation 330, the closer it is to the first electrode 324 or the second electrode 326, the stronger the EM field is. That is to say, the strongest EM field will be developed near the first electrode 324 and the second electrode 326. This field distribution would make a larger amount of light excited in areas near the first electrode 324 and the second electrode 326, and thus more light goes to the first electrode 324 and the second electrode 326, where the light is then reflected by the first electrode 324 and the second electrode 326.

The reflection of the light is achieved by the first electrode 324 and the second electrode 326 both of which are made of solid metal as mentioned above. In addition, because of the Far-UVC optical dielectric coating 338a, 338b attached to the interior sides of the first electrode 324 and the second electrode 326, the light as it is reflected is then filtered by the Far-UVC optical dielectric coating 338a, 338b back and forth in total two times as always. In this embodiment, Far-UVC light in a wavelength of 222 nm will be filtered out from other unwanted light having a wavelength above 230 nm by a certain percentage. In one specific implementation, the Far-UVC optical dielectric coating 338a, 338b act as a bandpass filter and are configured for filtering out Far-UVC radiations substantially in wavelengths in the range of 240 nm-280 nm. In this way, high purity of Far-UVC light can be obtained. In another implementation, the Far-UVC optical dielectric coating 338a, 338b filter at least one radiation having wavelengths that are in a range of between 180 nm to 240 nm, and facilitates a substantial power reduction of at least one radiation from having wavelengths outside of the range.

It should be noted that the reflection of Far-UVC light may happen multiple times between the first electrode 324 and the second electrode 326, because of the opposite positions of the first electrode 324 and the second electrode 326. However, eventually, the reflected and filtered light will leave the body 322 as shown by arrows 332 in FIG. 1, and emits as an output of the lamp 320 to the exterior environment, for example to a disinfection target like an object, a surface, or a human. The Far-UVC light leaves the body 322 because of the body 322 which is transparent to Far-UVC light.

Applying the same explanation of the mechanism of the lamp in the embodiment of FIGS. 3a-3b, the lamp 320 has a very high efficiency as compared to conventional Far-UVC excimer lamps because most of the excited light as they are generated near the reflective electrode can be reflected and outputted from the lamp 320 and more compact size to have shorter optimum distance. Thus, the disinfection time will be much shorter by a close infection distance comparatively, due to the theory of inverse law and lower propagation loss in the atmosphere of exterior environment. Hence, higher disinfection efficiency is achieved. It should be noted that no additional reflective component like a mirror is required compared to prior art. The compactness is also realized by the first electrode 324 simultaneously functioning as a heatsink (as it is made of solid material like aluminum), and this allows effective heat dissipation during the operation of the lamp 320, so that the separations between components of the lamp 320 can be reduced without the heat imposing any impacts to the stability and lifetime of these components.

Figure 5A:
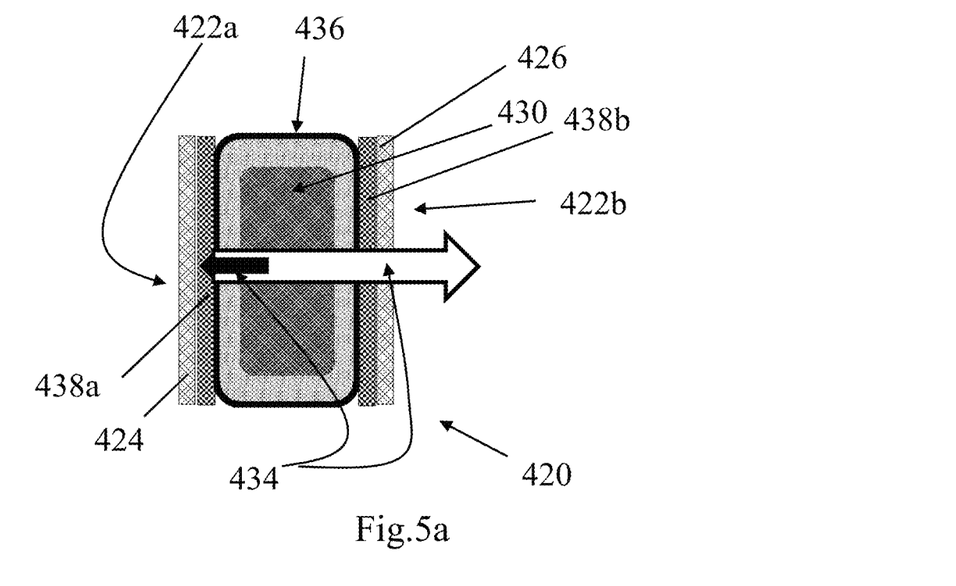
FIG. 5a is a cross-sectional view of a Far-UVC excimer lamp that includes transmissive dielectric coating filters attached to the interior side of a net metal electrodes, and a transmissive dielectric coating filters which is attached to the interior side of a Far-UVC reflective solid metal electrode, as well as working principle of the Far-UVC excimer lamp, according to a third embodiment of the invention.
Figure 5B:
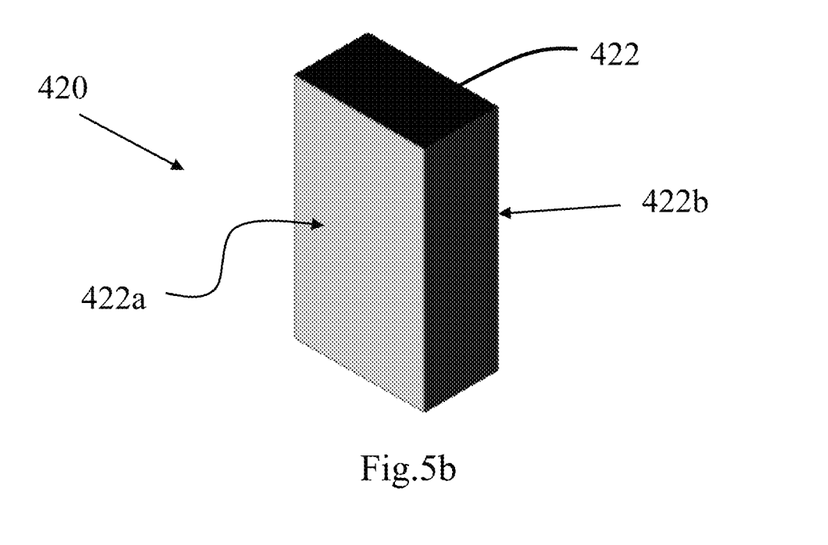

FIGS. 5a-5b show a Far-UVC excimer lamp 420 according to another embodiment of the invention, which combines advantages of the embodiment of FIG. 3a-3b and the embodiment of FIG. 4a-4b. In the embodiment of FIGS. 5a-5b, the first electrode 424 is made of net metal materials, but the second electrode 426 is made of solid metal material, and the material for the first electrode 424 and the material for the second electrode 426 can be the same or different. In one example, the first electrode 424 and the second electrode 426 are made of net aluminum and solid aluminum respectively. There is further a transmissive Far-UVC optical dielectric coating filter attached to the interior side of each of the first electrode 424 and/or the second electrode 426. The Far-UVC optical dielectric coating 438a is attached to the interior side of the first electrode 424, and the Far-UVC optical dielectric coating 438b is attached to the interior side of the second electrode 426. The first electrode 424 is located at a first end 422a of the body 422, and the second electrode 426 is located at a second end 422b of the body 422.

The working principle of the Far-UVC excimer lamp 420 of this embodiment can be seen as a combination of those of the embodiment in FIGS. 3a-3b and FIGS. 4a-4b. The first electrode 424 and the second electrode 426 are also energized by connecting an external power supply of the lamp 420, wherein the first electrode 424 or the second electrode 426 have alternating polarities. When the first electrode 424 and the second electrode 426 are energized, due to the electric field generated between the electrodes a discharge occurs, generating excimer molecules. When these excited molecules return to the ground state, high illumination Far-UVC light will emit out as the same explanation described before.

The Far-ultraviolet light as they are just generated in the main EM field area of radiation 430 travel generally toward the first electrode 424 and the second electrode 426, as shown by arrows 434 in FIG. 5a. In particular, the strongest EM field will be developed near the solid metal first electrode 424. This field distribution would make a larger amount of light excited in areas near the first electrode 424, and thus more light goes to the first electrode 424 and is then reflected by the first electrode 424 to the Far-UVC optical dielectric coating 438b attached to the interior side of the second electrode 426, then to the second electrode 426, and emitted out to the exterior environment.

The reflection of the light is achieved by the first electrode 424 which is made of solid metal as mentioned above. In addition, because of the Far-UVC optical dielectric coating 438a attached to the first electrode 424, the light as it is reflected is then filtered by the Far-UVC optical dielectric coating 438a by back-and-forth reflections in total two times. Afterwards, the reflected Far-UVC light will pass through the cavity 436 and reach the second electrode 426 which is attached the Far-UVC optical dielectric coating 438b at its interior side. The Far-UVC light exits the light source through the Far-UVC optical dielectric coating 438b and the second electrode 426, by another Far-UVC filtering. Therefore, a significant high percentage amount of Far-UVC emitted from the Far-UVC source will be employed three times of Far-UVC filtering, thus the outputted light will have a much higher purity of Far-UVC light quality compared to previous embodiments and prior arts as described.

Figure 6:
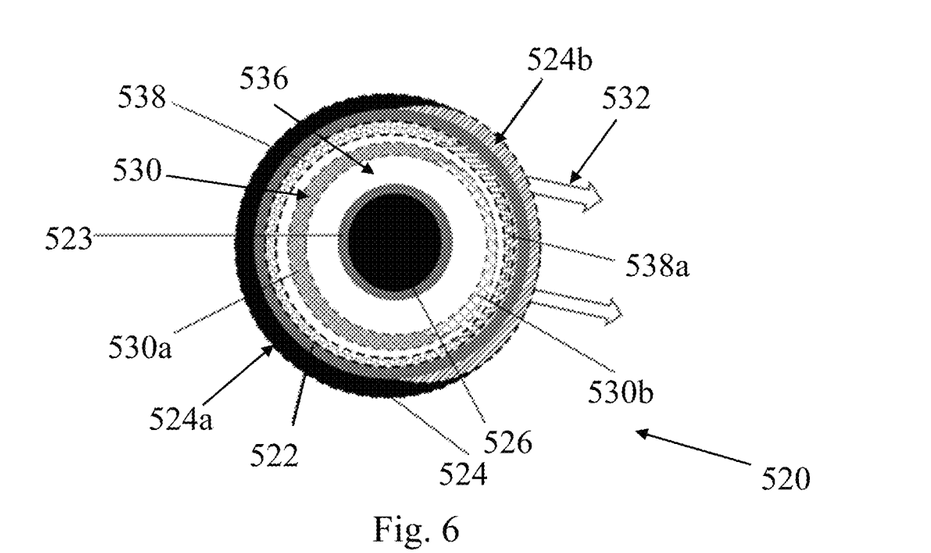
FIG. 6 is a cross-sectional view of a Far-UVC excimer lamp with a transmissive dielectric coating filter attached to the interior side of an outermost electrode, as well as working principle of the Far-UVC excimer, according to a fourth embodiment of the invention.

Turning to FIG. 6, which shows another embodiment of the invention which is a Far-UVC excimer lamp 520 that has a different structure as compared to previous embodiments, in that the lamp 520 contains two hollow tubes, namely a first tube part 122 and a second tube part 523. The first tube part 522 and the second tube part 523 are concentrically arranged and the first tube part 522 has a cavity size larger than that of the second tube part 523.

A cavity 536 is formed between the first tube part 522 and the second tube part 523, and the cavity 536 has a hollow cylindrical shape. As shown in FIG. 6, the first tube part 522 effectively encloses the second tube part 523 and the cavity 536. A second electrode 526 is located within the second tube part 523 and has a cylindrical shape. On the other hand, a first electrode 524 is located outside the first tube part 522 and has a square ring shape. Note that the first tube part 522 could be any cylinder shape including cylinder shape, rectangular cylinder shape or hexagon cylinder shape. One example of the shape of the first tube part 522 is a square column-shaped body, which will be cheaper in total cost as the dielectric coating filter is cheaper in cost if it is developed as a flat plate, rather than as a curved plate.

In particular, the first electrode 524 contains two parts, namely a first solid conductive metal part 524a and a second net conductive metal part 524b. The first solid conductive metal part 524a and the second net conductive metal part 524b each have a curved shape and span around 180 degrees along a circumferential direction. Together, the first solid conductive metal part 524a and the second net conductive metal part 524b constitute a complete circular shape of the first electrode 524. Each of the first solid conductive metal part 524a and the second net conductive metal part 524b has a shape that follows a shape of a part of the first tube part 522 in a circumferential direction. The first solid conductive metal part 524a of the first electrode 524 and the second electrode 226 are made of solid metal material, and the material for the first solid conductive metal part 524a and the material for the second electrode 526 can be the same or different. In one example both the first solid conductive metal part 524a and the second electrode 526 are made of solid aluminum. In comparison, the second net conductive metal part 524b is not made of solid metal, but as its name suggests is made of a metal net. There is further a filter attached to interior sides of the first solid conductive metal part 524a of the first electrode 524, and in particular a transmissive filtering coating or glass 538 is placed on the interior surface of the first solid conductive metal part 524a of the first electrode 524. On the interior surface of the second net conductive metal part 524b there is also a dielectric coating filter 538a disposed.

In the cavity 536, an excited molecule complex for example an exciplex such as either krypton-bromine (KrBr) or krypton-chlorine (KrCl) for Far-UVC is filled. As a result, a main EM field area of radiation 530 in excited gas can be defined in the cavity 536. However, the EM field in the cavity 536 is not uniform along the circumferential direction. Rather, because of the presence of the first solid conductive metal part 524a of the first electrode 524, a larger, stronger EM field area of radiation 530a is located near the first solid conductive metal part 524a, and has a shape substantially correspond to that of the first solid conductive metal part 524a. In comparison, a smaller EM field area of radiation 530b is located near the second net conductive metal part 524b. The larger EM field area of radiation 530a and the smaller EM field area of radiation 530b are formed because of the difference in achieving electrical fields by different electrodes, namely the first solid conductive metal part 524a and the second net conductive metal part 524b. The larger stronger EM field area of radiation 530a and the smaller stronger EM field area of radiation 530b together make up the main strongest EM field area of radiation 530.

Having described the structure of the Far-UVC excimer lamp 520, now the working principle of the Far-UVC excimer lamp 520 will be described. The first electrode 524 and the second electrode 526 are energized when they are connected to an external power supply of the lamp 520. The first electrode 524 and the second electrode 526 have alternating polarities. In particular, the second electrode 526 has a positive polarity and the first electrode 524 has a negative polarity. When the first electrode 524 and the second electrode 526 are energized, due to the electric field generated between them a discharge occurs, generating excimer molecules. When these excited molecules return to ground state, high-intensity Far UVC light is emitted. In this embodiment, the light emitted from the main EM field area of radiation 530 has a wavelength between 180-240 nm mainly.

As mentioned above, a relatively larger EM field area of radiation 530a will be developed more near the first solid conductive metal part 524a. It would make more light excited there as compared to smaller area of stronger EM field of radiation 530b. As a result, more excited light goes to the first solid conductive metal part 524a than those going to the second net conductive metal part 524b. Because the first solid conductive metal part 524a is reflective, and acts like a mirror, most of the excited light is then reflected by the first solid conductive metal part 524a and the moves toward the second net conductive metal part 524b. In addition, because of the dielectric coating filter 538 attached to the interior side of the first solid conductive metal part 524a and dielectric costing filter 538a attached to the interior side of the second net conductive metal part 524*b*, all the light emitted out from the Far-UVC source is filtered. Because the second net conductive metal part 524*b* is not a solid material but a metal net, the Far-UVC light will be able to pass through the second net conductive metal part 524*b* after passing through the body 522. In this way, eventually the reflected and filtered light will leave the body 522 as shown by arrows 532 in FIG. 6 and emits as output of the lamp 520 to the exterior environment, for example to a disinfection target. As more light is reflected by the first solid part to have an additional two times Far-UVC filtering, the purity of Far-UVC light is improved compare to Prior Arts design with only one time filtering.

In a variation of the above embodiment, the lamp could also be implemented by re-arranging the Far-UVC reflective type dielectric coating filter for attaching to the first electrode. As a result, more excited light still goes to the reflective dielectric coating filter 538*a* which is attached to the interior side of the first solid conductive metal part 524*a*, but will not reach the first solid conductive metal part 524*a*. The light will be reflected by the reflective dielectric coating filter 538*a* that acts like a mirror, most of the excited light is then reflected the moves toward the second net conductive metal part 524*b* through another transmissive dielectric coating filter 538*b* which is attached to the interior side of the second net part 524*b*. Therefore, all the light emitted out from the Far-UVC source is filtered, but only one filtering by the transmissive dielectric coating filter 538*b*. In this way, eventually the reflected and filtered light will leave the body 522 as shown by arrows 532 in FIG. 6 and emits as output of the lamp 520 to the exterior environment, for example to a disinfection target.

In this embodiment, Far-UVC light in a wavelength of 222 nm will be filtered out from other unwanted light having a wavelength above 230 nm by a certain percentage. In one implementation, the dielectric coating filter 538*a*, 538*b* acts as a bandpass filter and is configured for filtering out UVC radiations substantially in wavelengths in the range of 240 nm-280 nm.

At the same time the structure of the lamp 520 is quite compact and as no additional reflective component like a mirror is required. The compactness is also having the same advantage of higher illumination by close exposure disinfection, hence it achieves a shorter disinfection time, as explained in relation to previous embodiments.

Moreover, the compactness is realized by the first solid conductive metal part 524*a* simultaneously functioning as a heatsink (as it is made of solid material like aluminum), and this allows effective heat dissipation during the operation of the lamp 520, so that the separations between components of the lamp 520 can be reduced without the heat imposing any impacts to the stability and lifetime of these components.

Figure 7:
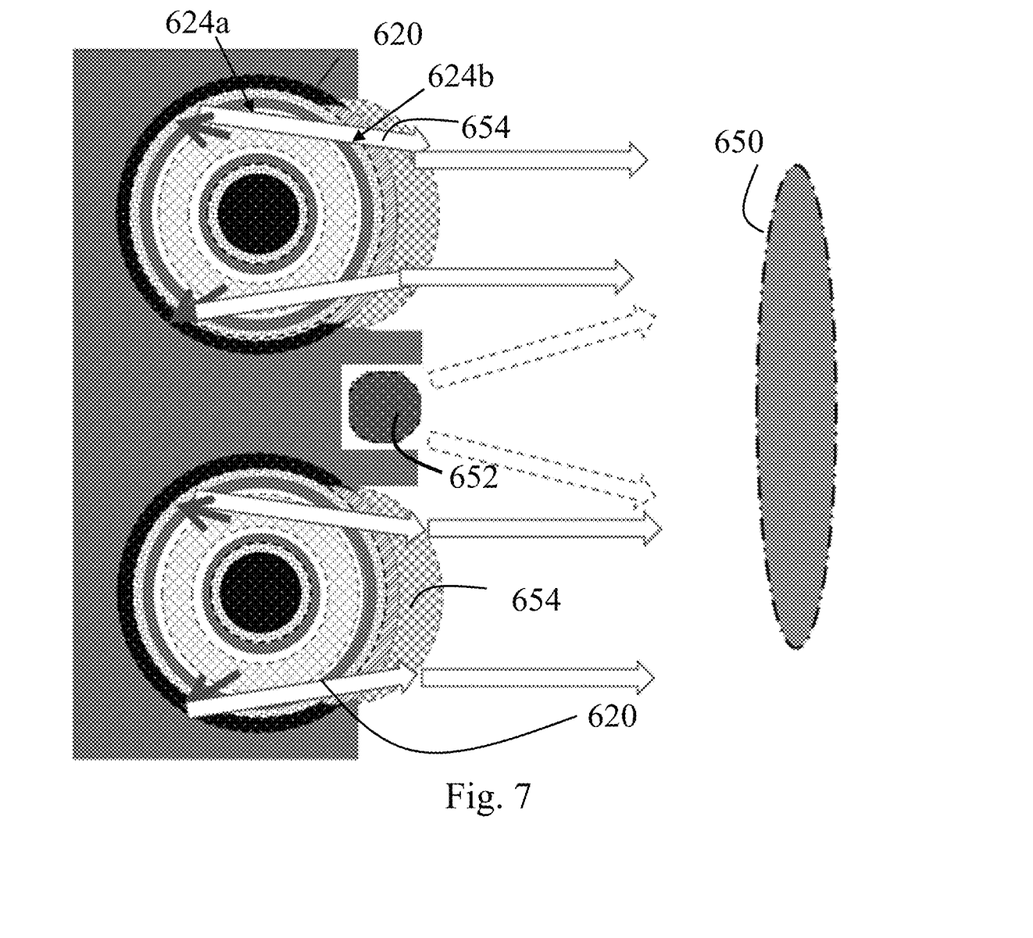
FIG. 7 is a cross-sectional view of a Far-UVC excimer lamp device including Far-UVC excimer lamps shown in FIG. 6, and working principle of the lamp device, according to a further embodiment of the invention.

Now turn to FIG. 7. Another embodiment of the invention is a Far-UVC excimer lamp device which contains two Far-UVC excimer lamps 620 and an infrared light source 652. Each of the lamps 620 has a structure similar to that as shown in FIG. 6, so the structure and function of the lamps 220 will not be described in detail here for the sake of brevity. A difference between the lamps 220 and that shown in FIG. 6, is that the proportion of the solid metal electrode 624*a* to the net metal electrode 624*b* is greater than that in FIG. 6. As shown in FIG. 7, the solid metal electrode 624*a* spans more than 180 degrees in the circumferential direction. In addition, an optical lens 654 is located outside each lamp 620 and in particular located outside the net metal electrode 624*b*. The optical lens 654 is configured for focusing the light emitted from the lamp 620.

It can be seen from FIG. 7 that the two Far-UVC excimer lamps 620 and the infrared light source 652 are aligned substantially along a straight line (not shown) such that light emission directions from the two Far-UVC excimer lamps 620 and the infrared light source 652 are substantially facing a same direction, and toward a disinfection target 650. The Far-UVC excimer lamp device shown in FIG. 7 has a compact structure to integrate the infrared light source 652 and the Far-UVC excimer lamp 620 together in order to have efficient exposure areas for all the light sources 652 on the disinfecting target 250. However, the solid metal electrode 624*a* in each lamp 620 acts like a heatsink for both the lamp 620 and block the light from infrared light source 652 towards the far-UVC lamps. In addition, the solid metal electrode 624*a* in each lamp 620 functions as a light block (as its circumferential spanning is more than 180 degrees as mentioned above) for avoiding any infrared light emitted to the lamp 620. Hence, the heat-sink electrode can dissipate the heat from the infra-light source. Therefore, the integration of the Far-UVC excimer lamp device shown in FIG. 7 has a compact structure to integrate the infrared light source 652 and the far-UVC excimer lamps 620 will not raise the temperature of the lamps 620 and good emission efficiency of the lamps 620 can be kept. Also, it would be easier to have a more compact Far-UVC excimer lamp with a heavy heat sink, in order to install a heating light supplementary apparatus (for example the infrared light source mentioned above), in order to further decrease the disinfection time for the target.

The exemplary embodiments are thus fully described. Although the description referred to particular embodiments, it will be clear to one skilled in the art that the invention may be practiced with variation of these specific details. Hence this invention should not be construed as limited to the embodiments set forth herein.

While the embodiments have been illustrated and described in detail in the drawings and foregoing description, the same is to be considered as illustrative and not restrictive in character, it being understood that only exemplary embodiments have been shown and described and do not limit the scope of the invention in any manner. It can be appreciated that any of the features described herein may be used with any embodiment. The illustrative embodiments are not exclusive of each other or of other embodiments not recited herein. Accordingly, the invention also provides embodiments that comprise combinations of one or more of the illustrative embodiments described above. Modifications and variations of the invention as herein set forth can be made without departing from the spirit and scope thereof, and, therefore, only such limitations should be imposed as are indicated by the appended claims.

The embodiment in FIGS. 3*a*-3*b* is shown to contain Far-UVC optical filtering dielectric coating placed at or near both of the two electrodes of the light source. However, those skilled in the art should understand that in other variations of the embodiments, it could be that the dielectric coating filter is located only at one of the electrodes, while the other electrode as no coating filter.

In the exemplary embodiments described above, the Far-UVC excimer lamp is a Far-UVC excimer lamp design to emit a Far-UVC radiation with a wavelength of about 220 nm. Those skilled in the art should understand the invention is not limited to Far-UVC lamps. Rather, any types of Far-UVC excimer lamps, no matter what the wavelength of the Far-UVC light is, may fall into the scope of the invention if an electrode is used also as a reflector.

Although not shown in the embodiments above, in variations of the embodiments a convex lens would be applied and/or attached to the excimer lamp in order to have emitted Far-UVC light further focused on the disinfection target so as to improve the disinfection efficiency of the lamp.

What is claimed is:

1. A Far-UVC excimer light source, comprising:
   a) a first electrode adapted to be energized;
   b) a second electrode adapted to be energized;
   c) a body defining a cavity that is filled with an excited molecule complex between the first and second electrodes; and
   d) a Far-UVC filter attached to an interior side of the first electrode and adapted to filter a Far-UVC light excited in the cavity of the body, wherein the Far-UVC filter is located inside the light source, between the cavity with the excited molecules and the first electrode.

2. The Far-UVC excimer light source of claim 1, wherein the Far-UVC filter attached to the interior side of the first electrode is a transmissive Far-UVC optical filtering dielectric coating or coated glass which is integrated, placed on or near the interior side of first electrode inside the light source.

3. The Far-UVC excimer light source of claim 1, wherein the Far-UVC filter is adapted to filter at least one radiation having wavelengths that are in a range of between 180 nm to 240 nm, and to facilitate a substantial power reduction of the at least one radiation from having wavelengths outside of the range.

4. The Far-UVC excimer light source of claim 2, wherein the Far-UVC optical filtering dielectric coating or coated glass comprises a dielectric coating of a dielectric material with a different refractive index to a substrate.

5. The Far-UVC excimer light source of claim 4, wherein the dielectric coating is constructed from dielectric material selected from the group of magnesium fluoride, calcium fluoride, and various metal oxides.

6. The Far-UVC excimer light source of claim 1, wherein the first electrode is at least partially made of a net metal to transmit the Far-UVC light through the Far-UVC filter, which is attached to the interior side of the first electrode inside the light source.

7. The Far-UVC excimer light source of claim 1, wherein the first electrode is at least partially made of a solid metal to reflect the Far-UVC light through the Far-UVC filter, which is attached to the interior side of the first electrode inside the light source.

8. The Far-UVC excimer light source of claim 1, wherein the molecules complex comprises at least one of a krypton-bromine gas or a krypton-chlorine gas.

9. The Far-UVC excimer light source of claim 1, wherein the body has a substantially elongated shape defining two ends; the first and second electrodes respectively located at the two ends within the body.

10. The Far-UVC excimer light source of claim 1, wherein the body comprises a first tube part and a second tube part that are concentrically arranged, such that the cavity is formed between the first and second tube parts and has a hollow cylinder shape; the first tube part enclosing the second tube part and the cavity; the second electrode located within the second tube part; the first electrode located outside the first tube part and having a shape that follows a shape of part of the first tube part in a circumferential direction.

11. The Far-UVC excimer light source of claim 10, wherein the first tube part has a cylinder shape, a rectangular cylinder shape or a hexagon cylinder shape.

12. A Far-UVC excimer light source, comprising:
   a) a first electrode adapted to be energized;
   b) a second electrode adapted to be energized;
   c) a body defining a cavity that is filled with an excited molecule complex between the first and second electrodes; and
   d) a first Far-UVC filter attached to the interior side of the first electrode and adapted to filter a Far-UVC light excited in the cavity of the body, wherein the first Far-UVC filter is located inside the light source, between the cavity with the excited molecules and the first electrode,
   e) a second Far-UVC filter attached to the interior side of the second electrode and adapted to filter a Far-UVC light excited in the cavity of the body, wherein the second Far-UVC filter is located inside the light source, between the cavity with the excited molecules and the second electrode.

13. The Far-UVC excimer light source of claim 12, wherein at least one or both of the first and second electrodes is partially made of a net metal to transmit the Far-UVC light through the first Far-UVC filter or the second Far-UVC filter attached on the interior side of the corresponding electrode.

14. The Far-UVC excimer light source of claim 12, wherein at least one or both of the first and second electrodes is partially made of a solid metal to reflect the Far-UVC light through the first Far-UVC filter or the second Far-UVC filter attached on the interior side of the electrode.

15. The Far-UVC excimer light source of claim 12, wherein the solid metal is chosen from the group consisting of stainless steel, aluminum, and copper.

* * * * *